(12) United States Patent
Darson et al.

(10) Patent No.: US 11,451,722 B2
(45) Date of Patent: Sep. 20, 2022

(54) ADAPTIVE OPTICS IMAGE ACQUISITION METHOD

(71) Applicants: CENTRE NATIONAL DE LA RECHERCHE SCIENTIFIQUE (CNRS), Paris (FR); SORBONNE UNIVERSITE, Paris (FR); ECOLE NORMALE SUPERIEURE, Paris (FR); UNIVERSITE DE PARIS, Paris (FR); UNIVERSITE DE BOURGOGNE, Dijon (FR); OBSERVATOIRE DE PARIS, Paris (FR)

(72) Inventors: David Darson, Vaux le Penil (FR); Julien Dubois, Quetigny (FR); Francois Colas, Paris (FR)

(73) Assignees: CENTRE NATIONAL DE LA RECHERCHE SCIENTIFIQUE, Paris (FR); SORBONNE UNIVERSITE, Paris (FR); ECOLE NORMALE SUPERIEURE, Paris (FR); UNIVERSITE DE PARIS, Paris (FR); UNIVERSITE DE BOURGOGNE, Dijon (FR); OBSERVATOIRE DE PARIS, Paris (FR)

( * ) Notice: Subject to any disclaimer, the term of this patent is extended or adjusted under 35 U.S.C. 154(b) by 0 days.

(21) Appl. No.: 17/277,462

(22) PCT Filed: Sep. 17, 2019

(86) PCT No.: PCT/FR2019/052160
§ 371 (c)(1),
(2) Date: Mar. 18, 2021

(87) PCT Pub. No.: WO2020/058623
PCT Pub. Date: Mar. 26, 2020

(65) Prior Publication Data

US 2021/0352229 A1 Nov. 11, 2021

(30) Foreign Application Priority Data

Sep. 20, 2018 (FR) ..................................... 1858510

(51) Int. Cl.
*H04N 5/345* (2011.01)
*H04N 5/232* (2006.01)
(Continued)

(52) U.S. Cl.
CPC ......... *H04N 5/345* (2013.01); *H04N 5/23222* (2013.01); *H04N 5/23229* (2013.01); *H04N 5/357* (2013.01); *H04N 5/374* (2013.01)

(58) Field of Classification Search
CPC ............... H04N 5/345; H04N 5/23222; H04N 5/23229; H04N 5/374; H04N 5/357
See application file for complete search history.

(56) References Cited

U.S. PATENT DOCUMENTS

2004/0190762 A1* 9/2004 Dowski, Jr. ........ G06K 9/00597
382/128
2005/0098707 A1 5/2005 Wirth
(Continued)

OTHER PUBLICATIONS

Written Opinion for PCT/FR2019/052160 dated Jan. 30, 2020.
International Search Report for PCT/FR2019/052160 dated Jan. 30, 2021.

*Primary Examiner* — Yogesh K Aggarwal
(74) *Attorney, Agent, or Firm* — Womble Bond Dickison (US) LLP

(57) ABSTRACT

The invention relates to a method for acquiring an image by an imager (20) comprising a matrix of pixels configured to generate an electric response when exposed to an incident light flux travelling through an optical path (21) in which is arranged a wavefront correction element (22), comprising the following steps:
1) initiating the exposure of the pixels to the incident light flux;

(Continued)

Figure 1:
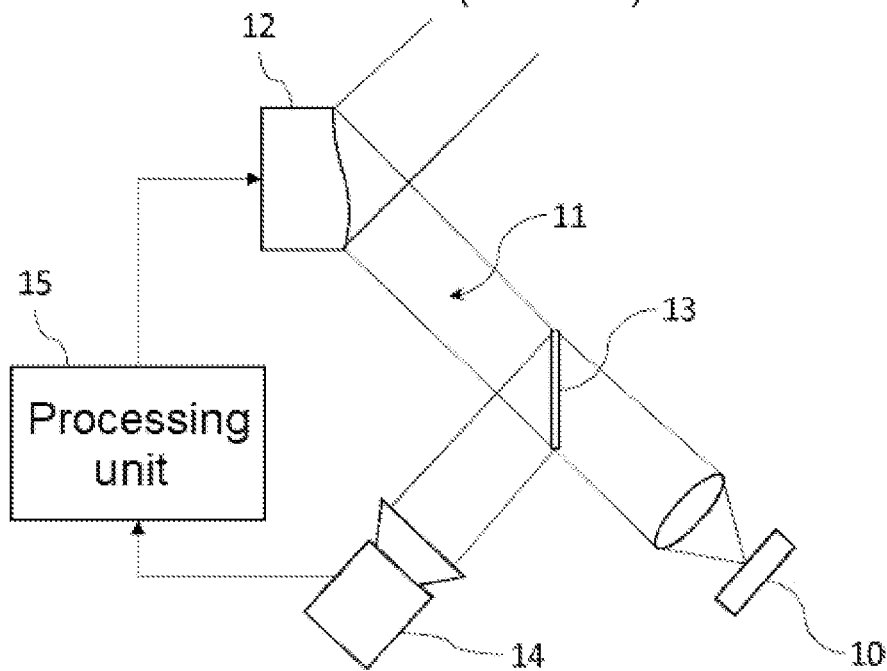

2) for a plurality of iterations during the exposure:
   2.1) non-destructive reading of the electric responses of pixels of a region of interest;
   2.2) determining an evolution of the spatial distribution of pixels in logarithmic mode previous iteration with respect to the previous iteration;
   2.3) based on said evolution, establishing a command for the wavefront correction element (22) in order to correct the wavefront;
   2.4) configuring the wavefront correction element,
3) reading the electric responses of the pixels resulting in an image.

13 Claims, 3 Drawing Sheets

(51) Int. Cl.
    *H04N 5/357*     (2011.01)
    *H04N 5/374*     (2011.01)

(56) References Cited

U.S. PATENT DOCUMENTS

| | | |
|---|---|---|
| 2013/0250240 A1 | 9/2013 | Kim |
| 2014/0270565 A1 | 9/2014 | Poyneer et al. |
| 2016/0349529 A1* | 12/2016 | Protz .................. G02B 27/644 |

\* cited by examiner

ADAPTIVE OPTICS IMAGE ACQUISITION METHOD

CONTEXT AND PRIOR ART

The present invention relates to the field of image acquisition by an imager. More precisely, the invention relates to a method for acquiring an image by an imager exposed to an incident light flux travelling through the optical path of an optical system comprising a wavefront correction element, in order to implement an adaptive optics technique.

The resolution of an optical system is closely linked to its capacity to separate the finest details of an object seen by an imager. In a perfect optical system with an aperture diameter D, the resolution is limited, according to the Rayleigh criterion, by the diffraction, at a minimum viewing angle between two details of $\Delta\phi = 1.44 \lambda/D$ (where $\lambda$ is the wavelength). In reality, many elements can degrade this theoretical separating power, or even the PSF (Point Spread Factor) also known as spatial impulse response of the system optics-imager firstly, all the optical defects and aberrations generated by the optical system itself but also all those coming from the propagation medium of the light. Although technical progress has made it possible to create optical systems with practically no intrinsic optical static defects or aberrations, it is still not possible to modify the dynamic characteristics whether of the opto-mechanical system itself or the propagation medium.

During its travel from a light source to an imager, a light flux undergoes distortions in its wavefront due to the disturbances of the propagation medium, resulting in particular in the inhomogeneity of said medium. Other than all the static defects, all the dynamic defects of the opto-mechanical system (dilatation-contraction, vibration, etc.) can also degrade the PSF of the group optics-imager. PSF which in a perfect system, without any defect or aberrations, is subjected only to the diffraction limit of the system considered.

For example, in astronomy, the one-off light from a star propagates in a straight line, in a vacuum, to the Earth. The wavefront of the light flux is then a plane and remains a plane in the vacuum, in principle capable of giving a spot limited by diffraction in a telescope that would receive this light, which is the case of the various telescopes placed in orbit in the vacuum of space.

However, in the case of an imager such as a telescope on the ground of the Earth, the light flux also travels through the terrestrial atmosphere. The atmosphere is constituted of gases of which the composition and especially the density varies in time and space, and therefore has refractive index fluctuations, which results in the atmospheric turbulences that the light flux is subjected to.

Likewise, in the field of eye imaging, our eyes are constantly moving; even when staring, our eyes are agitated by involuntary movements. These movements, called fixation, are indispensable for vision, because they make it possible to maintain visual perception. Thus, the mediums travelled through by the light flux are in movement. In addition, the lighting light flux travels through several media (the cornea, the crystalline lens, or the vitreous body) that have varied compositions, densities and reduction indexes, which can alter the wavefront. Other dynamic aberrations can also occur, for example due to the micro-accommodations of the crystalline lens or to the flow of the tear film.

This results that in most applications, the characteristics of the propagation medium of the light flux vary constantly. This results in distortions in the wavefront of the light flux, which also vary, and in particular which vary during the exposure of the imager in the process of acquiring an image. The size of the diffraction spot at the imager increases considerably, degrading the PSF and consequently lowering the resolution of the image acquired by this imager. The longer the exposure is prolonged during the acquisition of an image, the more accentuated the effect is.

To improve the quality of the images acquired, solutions have been developed to measure and compensate the distortions of the wavefront of the incident light flux. One of these solutions is adaptive optics, which makes it possible to correct in real time the changing and non-predictive deformations of the wavefront FIG. 1 shows a typical example of an optical system of the prior art implementing an adaptive optics technique.

The system then comprises an imager 10 that receives light via an optical path 11. The optical path 11 comprises a wavefront correction element 12 (typically a deformable mirror) downstream of a beam splitter 13. The beam splitter 13 deviates a portion of the light flux to a device for measuring the wavefront 14 (a wavefront analyser, for example a sensor of the Shack-Hartmann type). A control loop comprising a data processing unit 15 uses the measurement from the device for measuring the wavefront 14 to determine the command of the wavefront correction element 13. According to this command, the configuration of the wavefront correction element 13 is modified in order to correct the wavefront of the light flux travelling the optical path 11 before the arrival thereof on the imager 10.

Such a system therefore requires two image taking devices: the imager 10 that has to acquire the image, and the device for measuring the wavefront 14 that has to measure the distortions of the wavefront. This results in a complexity of the system and substantial bulkiness. In addition, as the two image taking devices are spatially distant, different mechanical constraints can appear in terms of disturbances to which these devices are subjected such as for example vibrations.

Moreover, the presence of the beam splitter 13 dividing the light flux implies that the imager 10 receives only a portion of this light flux when it acquires an image, which makes a longer exposure time required in order to compensate the deviation of a portion of the light flux, increasing the problems of variation of the light flux, and can even prevent the imaging of certain objects that are not very bright, which for example would no longer be sufficiently distinguished from the measurement noise.

Systems that implement adaptive optics without using a dedicated device for measuring the wavefront have therefore been developed: it is the imager that collects the data used to analyse the wavefront. More precisely, the first images acquired by the imager are used to determine the command to be applied to the wavefront correction element 13. Thus, the first images are destroyed in order to determine the correction to be applied. Moreover, this approach assumes that the distortions of the wavefront vary little during the acquisition of an image, since it is the correction determined from the preceding image that is used. It is therefore necessary for the correction to remain within the coherence time of the turbulence considered, which involves sufficiently increasing the acquisition rate, in terms of images per second, which decreases by as much the signal that can be used on the individual images. Some systems combine the imager and the device for measuring the wavefront in the same matrix. This results in a loss of resolution of the acquired images, although the adaptive optics aims to improve the resolution.

PRESENTATION OF THE INVENTION

The invention has for purpose to allow for the acquisition of an image that has an improved resolution, and an increase in the signal to noise ratio (SNR) consecutive to the improvement of the PSF, by the correction of the wavefront of the incident light flux during the exposure, without loss of light flux or exposure time, and without requiring a device for measuring the wavefront that is specifically dedicated to the analysis of the distortions of the wavefront.

For this purpose, a method is proposed for acquiring an image by an imager comprising a matrix of pixels configured to generate an electric response when exposed to an incident light flux travelling through an optical path in which is arranged a wavefront correction element, the imager being adapted to allow for a non-destructive reading of the electric response of pixels during the exposure, the method comprising the following steps:

1) initiating the exposure of the pixels of the matrix of pixels to the incident light flux;
2) for a plurality of iterations during the exposure of the pixels:
   2.1) non-destructive reading of the electric responses of pixels of a region of interest;
   2.2) determining an evolution of the spatial distribution of pixels in logarithmic mode previous iteration with respect to the previous iteration on the basis of the electric responses of the pixels of the region of interest, representative of a fluctuation in a wavefront of the incident light flux between this iteration and the previous iteration;
   2.3) based on said evolution, establishing a command for the wavefront correction element in order to correct the wavefront of the light flux;
   2.4) configuring the wavefront correction element through the command,
3) reading the electric responses of the pixels of the matrix of pixels resulting in an image.

The method is advantageously supplemented by the following characteristics, taken individually or in any technical permissible combination:

the method comprises a prior step of resetting pixels of the matrix before step 1);
determining the evolution of the spatial distribution of pixels in logarithmic mode comprising identifying said pixels in logarithmic mode, said identifying comprising a comparison between each one of the electric responses and a threshold, the crossing of the threshold value by the electric response of a pixel indicating that said pixel is in logarithmic mode;
determining the evolution of the spatial distribution of pixels in logarithmic mode comprises identifying pixels in logarithmic mode and a comparison between positions of these pixels in logarithmic mode with positions of pixels in logarithmic mode during the previous iteration;
determining the evolution of the spatial distribution of pixels in logarithmic mode comprises identifying a contour that separates the pixels in logarithmic mode and the pixels in linear mode, and the comparison between the position of the contour and the preceding position of the contour during the previous iteration;
the command of the wavefront correction element is determined so as to stabilise the spatial distribution of pixels in logarithmic mode between two iterations;
the region of interest groups together less than half of the pixels of the matrix;
the method comprises at least five iterations implementing steps 2.1) to 2.4);
the region of interest is defined prior to the exposure of the pixels;
the method comprises a prior step of identifying the region of interest intervening between step 1) and step 2), wherein the region of interest is determined after a non-destructive reading step of the electric responses of all the pixels, the region of interest being defined to group together a set of pixels having electric responses on the average greater than electric responses of the pixels outside the region of interest;
during step 2.1), the electric responses of the other pixels outside the region of interest are not read.

The invention also relates to a computer program product comprising program code instructions recorded on a non-transitory medium that can be used in a computer for the execution of the steps of a method according to the invention when said program is executed on a computer using said non-transitory medium.

The invention also relates to an image acquisition system comprising:

an imager comprising a matrix of pixels in photovoltaic mode configured to generate an electric response when exposed to an incident light flux, the imager being adapted to allow for a non-destructive reading of the electric response of pixels during the exposure,
an optical path leading to the imager,
a wavefront correction element arranged in the optical path downstream from the imager,
a data processing unit configured to implement steps 2.1) to 2.4) according to the invention.

PRESENTATION OF THE FIGURES

Figure 2:
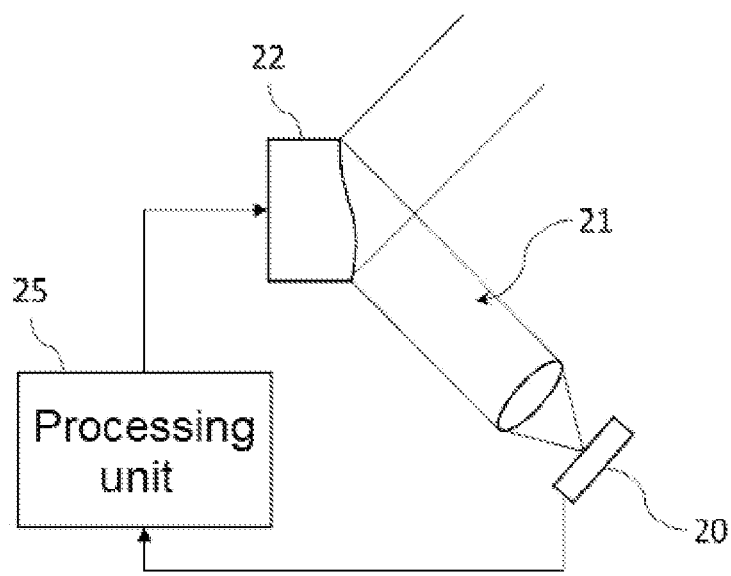
Figure 3:
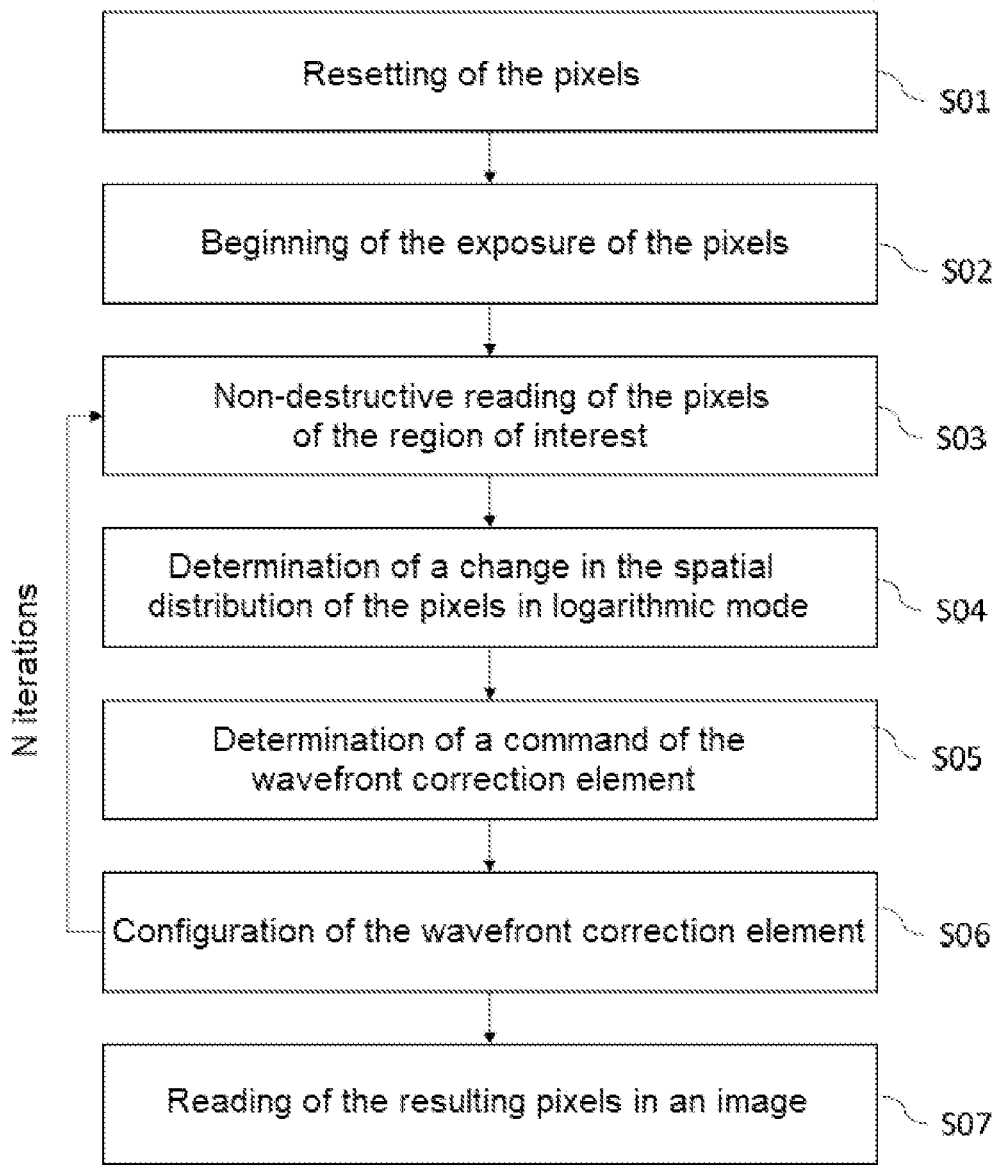
Figure 4:
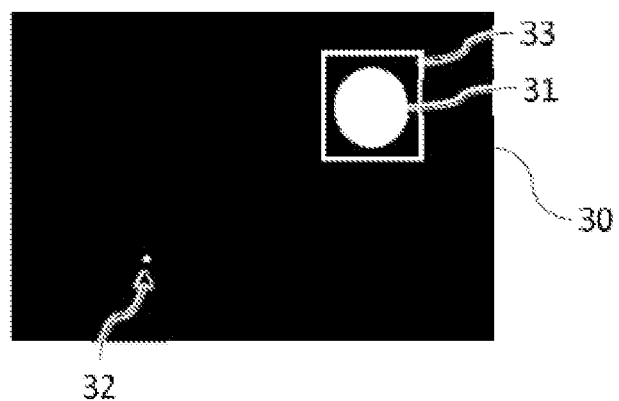
Figure 5A:
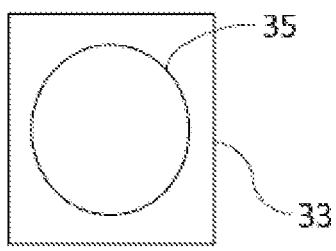
Figure 5B:
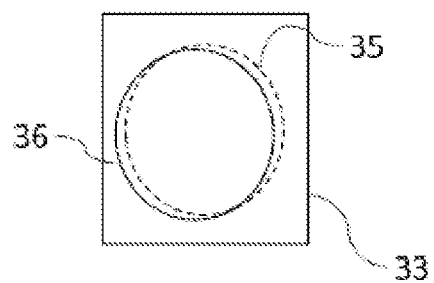

The invention will be better understood, thanks to the description hereinafter, which relates to embodiments and alternatives according to the present invention, given by way of non-limiting examples and explained in reference to the accompanying diagrammatical drawings, wherein:

FIG. 1, already commented, schematically shows an optical system of the prior art, FIG. 2 schematically shows an optical system according to a possible embodiment of the invention, FIG. 3 is a diagram showing steps of the method according to a possible embodiment of the invention, FIG. 4 is a diagram showing an example of an acquisition field of the imager and a region of interest, FIGS. 5a and 5b schematically show an example of an evolution of the spatial distribution of pixels in logarithmic mode between two iterations.

DETAILED DESCRIPTION

As the embodiments described in what follows are in no way limiting, it is possible in particular to consider alternatives of the invention that comprise only a selection of the characteristics described or illustrated isolated from the other characteristics described or illustrated (even if this selection is isolated within a sentence comprising these other characteristics), if this selection of characteristics is sufficient to confer a technical advantage or to differentiate the invention in relation to the prior art. This selection can include at least one characteristic more preferably functional without structural details, and/or with only a portion of the structural details if this portion only is sufficient to confer a technical advantage or to differentiate the invention in relation to the prior art.

In reference to FIG. 2, the method of acquisition is implemented by an image acquisition system comprising:
- an imager 20 comprising a matrix of pixels adapted to allow for a non-destructive reading of the electric response of pixels during the exposure,
- an optical path 21 leading to the imager 20,
- a wavefront correction element 22 disposed dans the optical path 21 downstream from the imager 20,
- a data processing unit 25.

The term imager 20 means an image taking device that can acquire an image, i.e. to render spatial distribution information of light intensity from an incident light flux to which the imager 20 is exposed. By way of a non-limiting example, an imager 20 can be used that offers possibilities similar to the NSC1601T-SI sensor from New Imaging Technologies at Verrières-le-Buisson, France, which is an InGaAs sensor based on a CMOS technology comprising a matrix of active pixels with a pitch of 15 μm with a global shutter, having a readout integrated circuit (ROIC) architecture that allows for different modes of destructive and non-destructive reading, such as for example ITR/IWR (Integrate Then Read/Integrate While Read), with a spectral response of 0.9 to 1.7 μm with a typical dynamic range greater than 120 dB, for an image frequency of up to 350 images per second.

The imager 20 comprises a matrix of active pixels each comprising, in the function of detecting and converting the light flux into an electric signal, by a photodiode used in photovoltaic mode: allowing in addition an intrinsic logarithmic response according to the instantaneous incident light flux, a linear response coming from its junction capacity as long as the latter is not saturated. The matrix is adapted to allow for the reading of the electric response of the pixels, whether the latter are in linear or logarithmic mode. Under the effect of a light flux, charge carriers (electron-hole pairs) are generated in the PN junction. The electrical voltage at the terminals of the photodiode then changes by a variation $V_D$:

$$V_D = V_T \ln \frac{I_\lambda + I_S}{I_\lambda e^{\frac{-(I_\lambda + I_S) \times t}{V_T C_D}} + I_S} \text{ with } V_T = \frac{kT}{q},$$

k the Boltzmann constant, T the temperature in K, q the elementary charge, t the exposure time, $I_S$ the saturation current of the junction of the photodiode, $I_\lambda$ the photocurrent, and $C_D$ the junction capacity.

According to the configuration of the pixel, the electric response can have various values. For example, the photodiodes of the pixels can initially be in reverse bias, with an initial voltage installed in the photodiode during the reset prior to the exposure. This initial voltage can make it possible to determine the range of use of the photodiode, and more precisely to adjust the passage from the linear mode to the logarithmic mode, according to the luminosity to which it is subjected and conditions for the usage thereof that follow this initialisation.

During the exposure, the photoelectric current induced in the photodiode by the charge carriers discharges the voltage progressively in the photodiode. At the beginning of exposure, as the quantity of light received is low, the photodiodes remain in reverse bias, with electric responses of the pixels that vary linearly:

$$V_D = -\frac{I_\lambda \times t}{C_D}$$

These pixels are said to be in linear mode.

When the exposure is prolonged, the photodiodes of the pixels receiving a strong light flux are completely discharged. The pixels then saturate. When a pixel saturates, its electric response in voltage at the terminals of its photodiode becomes a logarithmic response and varies according to:

$$V_D = V_T \ln \frac{I_\lambda + I_S}{I_S}$$

These pixels are then said to be in logarithmic mode.

The incident light flux travels along the optical path 21 to arrive at the imager 20. Contrary to the optical path 11 of a system of the prior art, this optical path 21 does not need to have a beam splitter 13 to deviate a portion of the light flux to a device for measuring the wavefront 14 dedicated to the analysis of the distortions of the wavefront. All of the incident light flux, except for the different losses inherent to the passage in the propagation mediums and in the optics, can reach the imager 20. Consequently, the imager 20 receives a larger quantity of light flux. The exposure time can thus be reduced, which avoids many problems.

The wavefront correction element 22 arranged in the optical path 21 downstream from the imager 20 corrects the wavefront of the incident light flux before the latter reaches the imager 20. The wavefront correction element 22 is typically, for example, an electromechanical microsystem, such as a deformable mirror. Such a deformable mirror is for example formed from a plurality of actuators under the mirror, flexible reflective surface. By modifying the position of the actuators, the surface of the mirror is modified, and therefore its configuration. The light flux arriving on the deformable mirror is not reflected in the same way over the entire flux, and the wavefront is modified. The surface of the deformable mirror can therefore be modified to correct the distortions of the wavefront. Other wavefront correction elements 22 are however possible, for example using liquid crystals.

In order to modify its configuration, the wavefront correction element 22 receives a command from the data processing unit 25. The data processing unit 25 typically comprises a processor and a memory, and is adapted to receive data (for example measurements), process them and to send data (for example a command). The data processing unit 25 is operationally connected with the imager 20 and with the wavefront correction element 22 so as to be able to communicate data with the imager 20 and the wavefront correction element 22. The data processing unit 25 can be composite, formed of several subsystems that each provide a portion of the functionalities of the data processing unit 25. The data processing unit 25, can be autonomous with its onboard system or also have a human-machine interface that makes it possible to enter data and to display it, comprising for example a keyboard and a screen.

In reference to FIG. 3, the method of acquiring an image by the imager 20 comprises several steps. The method can include a prior step (S01) of resetting pixels of the matrix of pixels of the imager 20. This reset consists in activating a reset signal. The reset signal makes a reset transistor conductive and creates an electric path that imposes an initial voltage on the photodiodes of the pixels. Once the reset is performed, the reset signal is deactivated, and the electric path is interrupted. The exposure of the pixels of the matrix of pixels to the incident light flux then begins (step S02). The light flux travelling the optical path 21 and reaching the imager 20 modifies the electric responses of the pixels, as explained hereinabove.

During exposure, the method implements a plurality of iterations so as to correct the wavefront of the incident light flux. During each one of these iterations, the same steps are repeated. The first step (step S03) of the iteration comprises a non-destructive reading of the electric responses of pixels of a region of interest. It is the imager 20 that implements this non-destructive reading. A non-destructive reading is a reading that makes it possible to measure the electric response of a pixel without substantially modifying the electrical characteristics of the pixel. In particular, a non-destructive reading does not involve evacuating the charges accumulated in the pixel, and it does not involve resetting the pixel (no reset).

A region of interest is a set of pixels adjacent to one another. The region of interest can comprise several sets of pixels adjacent to one another. The region of interest can group together all the pixels of the matrix of the imager 20. However, the region of interest preferably groups together only a portion of the pixels of the matrix. Preferably, the region of interest groups together less than half of the pixels of the matrix, and preferably less than 20% of the pixels of the matrix, and preferably less than 10% of the pixels, even less than 5% of the pixels of the matrix. The electric responses of the other pixels outside the region of interest are not read. The other pixels outside the region of interest continue to accumulate the electric signal coming from the conversion of the incident light flux, during non-destructive reading.

Preferably, the method comprises at least five iterations, more preferably at least ten iterations, and even more preferably at least twenty iterations. In fact, as many iterations as possible will be implemented during the exposure. Indeed, the iterations ail to correct the distortions of the wavefront, and the more iterations there are during the exposure, the better the correction will be. It is moreover preferable that the period of the iterations be less than the variation period of these distortions. In the case of distortions that are the consequence of atmospheric turbulence, this is referred to as coherence time of the atmospheric turbulence. The number of iterations that it is possible to implement, and their rate, number per second, depends on the reading capacities of the imager 20, and especially the size of the region of interest. For example, when the imager has a reading capacity of 300 images per second (often designated by FPS for "frames per second"), this means that it can read a number of pixels equivalent to all its pixels 300 times per second. Thus, in the case of an imager 20 of 320 pixels by 256 pixels (i.e. 81,920 pixels) with 300 FPS, the imager 20 can perform 24,576,000 readings of pixels per second.

By limiting the size of the zone read, it is therefore possible to read this zone more often since less pixels will be read while still preserving the bandwidth in pixels per second of the imager 20. Taking the example hereinabove again, reading only the pixels of a region of interest grouping together only 10% of the pixels of matrix reverts to reading only 8,192 pixels at each reading. In light of the reading capacity of 24,576,000 pixels per second, the region of interest can be read 3,000 times per second. It is therefore observed that the reading speed of the region of interest is ten times greater than the reading speed of the complete matrix. Consequently, the number of iterations can be all the more so high as the region of interest is small. In the example hereinabove, a region of interest of 10% of the matrix allows for example the implementation of ten times more iterations than with the entire matrix read, for the same exposure time.

Moreover, the reasoning disclosed hereinabove is in accordance with the maximum reading speed of the imager 20. However, the exposure of the pixels is practically always longer (even much longer) than the minimum period allowed by the reading capacity of the sensor. Taking again the sensor of the example hereinabove, and assuming an exposure duration of 30 seconds (for example in astronomy), nearly 90,000 iterations of the method can be implemented during the exposure. In any case, the method comprises during the acquisition of an image preferably at least iterations, and preferably at least 20 iterations, and more preferably at least 100 iterations.

It is to be noted that a limit however resides in the capacity of the other components of the system to implement their respective functions during an iteration. However, a wavefront correction device 22 typically has a response period less than a few tens of milliseconds, and a simple data processing unit 25 can calculate much faster than is required. The imager 20 is therefore generally the limiting factor.

The region of interest preferably groups together the pixels that receives the largest quantity of light during the exposure, i.e. the pixels for which the incident light flux is the most substantial. The region of interest can be defined prior to the exposure of the pixels. For example, if the user knows beforehand the spatial distribution of the light intensity in the acquisition field of the imager 20, the user can delimit a region of interest that corresponds to the zone that will receive the most light. Prior knowledge of the spatial distribution of the light intensity can for example come from a previously-acquired image.

Alternatively, the method can comprise a prior step of identifying the region of interest intervening between the beginning of the exposure and the first iterations, wherein the region of interest is determined after a non-destructive reading step of the electric responses of all the pixels. The region of interest is defined to group together a set of pixels having electric responses on the average greater than electric responses of pixels outside the region of interest. In this region of interest, under light conditions that are globally constant during the exposure, except for the changes coming from corrections to be made, the more substantial light flux will cause the pixels to transit more quickly in the logarithmic response after saturation of the linear response and thus will offer a response in real time, sampled at the rate of the non-destructive readings, which will be according to the instantaneous incident light flux.

FIG. 4 shows as a non-limiting example an acquisition field 30 for an imager 20 in the field of astronomy. In this acquisition field 30 is a first object 31 that is very bright, and a second object 32 that is not bright. The pixels of the zone of the matrix receiving the light flux from the first object 31 receive a quantity of light that is much more substantial than the pixels of the zone of the matrix receiving the light flux from the second object 32. The region of interest is therefore chosen as comprising pixels of the zone of the matrix receiving the light flux from the first object 31. Preferably, the region of interest encompasses all the pixels of the zone of the matrix receiving the light flux from the first object 31. A user acquiring this image knows the position of the first object 31, and can therefore define the region of interest 33 beforehand. Lacking prior knowledge, it is easy to distinguish the position of the first object 31 thanks to its strong light intensity at the start of the exposure, and therefore to define the region of interest on the basis of a non-destructive reading of all the pixels at the beginning of the exposure.

The non-destructive reading of the electric responses of pixels of a region of interest makes it possible to collect the electric responses, typically the voltages of each one of the pixels or the variations thereof. At each iteration, a partial image is then obtained that corresponds only to the pixels of this region of interest. On the basis of the electric responses of the pixels of the region of interest, an evolution of the spatial distribution of pixels in logarithmic mode previous iteration with respect to the previous iteration is determined (step S04). In practice, the imager 20 transmits the results of the non-destructive readings, i.e. the partial image to the processing unit 25, and it is the processing unit 25 that determines the evolution of the spatial distribution of pixels in logarithmic mode.

As explained hereinabove, the pixels that receive the most light saturate and switch to logarithmic mode, while the other pixels remain in linear mode. In the example shown, the pixels that correspond to the first object 31 will quickly saturate and switch to logarithmic mode, while the pixels that correspond to the second object 32 remain in linear mode. Although a linear response only indicates the quantity of light to which a pixel has been subject since the beginning of the exposure, a logarithmic response translates in real time the force of the light flux to which the pixel is subjected at the time of the reading.

Thus, a pixel that has been subjected to a strong light flux and which has reached saturation remains saturated even if it no longer receives any light. If it receives light, its response will be a logarithm function of the light flux to which the pixel is exposed at the time of reading. The spatial distribution of the pixels in logarithmic mode therefore follows the instantaneous spatial distribution of the light flux to which the pixels are subjected. This instantaneous spatial distribution varies according to iterations, mainly due to the distortions of the wavefront. Without adequate correction of the wavefront, this results in a displacement of the spatial distribution of the intensity of the light flux. In the example of FIG. 4, the light flux coming from the first object 31 is displaced on the surface of the matrix of the imager 20. This displacement is shown in FIGS. 5a and 5b.

In FIG. 5a, the shape 35 groups together the pixels in logarithmic mode in the zone of interest 33 for the reading of iteration n. These are pixels receiving the light coming from the first object 31 at the time of the non-destructive reading of this iteration n. This shape 35 therefore corresponds to the position of the first object 31 perceived by the imager 20, i.e. the position on the partial image, at the time of the iteration n. In FIG. 5b, the shape 36 groups together the pixels in logarithmic mode in the zone of interest 33 for the reading of iteration n+1. They are pixels receiving the light coming from the first object 31 at the time of the non-destructive reading of the iteration n+1. This shape 36 therefore corresponds to the position of the first object 31 perceived by the imager 20 at the time of iteration n+1. The shape 35 is delimited by dashes in FIG. 5b. It is observed that the shape 36 has moved with respect to the shape 35. This reveals the fact that the spatial distribution of the pixels in logarithmic mode has changed between iteration n and iteration n+1, and therefore that the instantaneous spatial distribution of the light flux to which the pixels are subjected, has changed in a similar way between iteration n and iteration n+1. Thus, the position of the first object 31 perceived by the imager 20 has changed between iteration n and iteration n+1. Likewise, the first object 31 perceived by the imager 20 can have distortions that vary with the iterations, which also results in a change in the instantaneous spatial distribution of the light flux.

However, this change in the instantaneous spatial distribution of the light flux is mainly due to the distortions of the wavefront by the atmospheric turbulence or to any other variation, vibrations for example, in the optical path 21 between two iterations. Consequently, the evolution of the spatial distribution of the pixels in logarithmic mode is representative of a fluctuation in a wavefront of the incident light flux between iteration n and iteration n+1. A command of the wavefront correction element 22 can be determined (step SOS) by the processing unit 25 that receives the results of the non-destructive readings coming from the imager 20 so as to compensate this change in the spatial distribution, i.e. so as to compensate the displacement of the contour between iteration n and iteration n+1.

In detail, determining the evolution of the spatial distribution of pixels in logarithmic mode can comprise identifying said pixels in logarithmic mode among the pixels of the zone of interest of which the responses were read during the iteration. To do this, the identification can comprise a comparison between each one of the electric responses of these pixels and a threshold, the crossing of the threshold value by the electric response of a pixel indicating that said pixel is in logarithmic mode. As explained hereinabove, a pixel switches to logarithmic mode only when it becomes saturated. Before this saturation, the electric response is linear and increases with the exposure to the flux up to a saturation value. By placing the threshold slightly above this saturation value, it is possible to discriminate the pixels in logarithmic mode from the pixels in linear mode. Identifying pixels in logarithmic mode at each iteration makes it possible to determine the change in their spatial distribution, and therefore to determine a command of the wavefront correction element 22.

Determining the evolution of the spatial distribution of pixels in logarithmic mode can then comprise identifying pixels in logarithmic mode and a comparison between positions of these pixels in logarithmic mode with positions of pixels in logarithmic mode during the previous iteration. All the positions of the pixels in logarithmic can be used during the comparison. The comparison can also be restricted to only a portion of the pixels in logarithmic mode, of which the positions have an increased interest. This is in particular the case for pixels that belong to a contour separating pixels in logarithmic mode and pixels in linear mode.

In fact, determining the evolution of the spatial distribution of pixels in logarithmic mode can comprise identifying a contour that separates the pixels in logarithmic mode and the pixels in linear mode, in particular after identification of the pixels in logarithmic mode. In FIG. 5a, this contour corresponds to the edge of the shape 35, and to the edge of the shape 36 in FIG. 5b. Determining the evolution of the spatial distribution of pixels in logarithmic mode can then comprise the comparison between the position of the contour at one iteration (for example iteration n) and the preceding position of the contour during the previous iteration (for example iteration n+1), which corresponds to the evolution of the spatial distribution of the pixels in logarithmic mode making it possible to determine the command.

Entailing a partial image (restricted to the region of interest), it is possible to use various detection and segmentation methods used in imaging, such as for example, a simple selection of the response of all or of a portion of the pixels of the partial image of the previous iteration of which the luminance is located in the logarithmic response of the imager 20. A spatial pattern is then obtained. This selection is then followed by a search for this spatial pattern in the image of the current iteration. More sophisticated segmentation methods including a prior knowledge of the shape of the object to be detected can be considered (such as for example a disc in the case of a first object 31 corresponding to a star). These methods can consider all of the pixels of the zone of interest or only those for which the luminance is located in the logarithmic response of the sensor.

In any case, the command of the wavefront correction element is determined so as to stabilise the spatial distribution of pixels in logarithmic mode between two iterations that follow one another. This command, determined by the processing unit 25, is sent to the wavefront correction element 22. The configuration of the wavefront correction element 22 is modified according to the command (step S06). For example, if the wavefront correction element 22 is a deformable mirror, the orientations of the various mirror elements are modified in order to correct the wavefront.

This process is reiterated for each iteration (there may not be any comparison during the first iteration), so that the correction follows the variations of the distortions of the wavefront. Thus, the light flux arriving on the imager 20 is constantly corrected during the exposure, based on the use of the region of interest 33. At the end of the method, when the exposure is deemed as sufficient, and several iterations have been carried out during the exposure, the electric responses of the pixels of the matrix of pixels are read (step S07) resulting in an image. Taking again the example of FIG. 4, using pixels from the region of interest 33, saturated by the first object 31, makes it possible to acquire an image including a very high quality representation of the object 32, the light flux being constantly corrected and allowing in the zones of the image still in linear response a substantial increase in the signal to noise ratio and in the resolution due to the improvement in the PSF during the accumulation of the signal during the exposure between two resets of the pixels of the imager.

The invention is not limited to the embodiment described and shown in the accompanying figures. Modifications remain possible, in particular from the standpoint of constituting various technical characteristics or by substitution of technical equivalents, without however leaving the scope of protection of the invention.

The invention claimed is:

1. Method for acquisition of an image by an imager comprising a matrix of pixels configured to generate an electric response when exposed to an incident light flux travelling through an optical path in which is arranged a wavefront correction element, the imager being adapted to allow for a non-destructive reading of electric responses of pixels during the exposure, the method comprising:
   1) initiating an exposure of the pixels of the matrix of pixels to the incident light flux;
   2) for a plurality of iterations during the exposure of the pixels:
   2.1) non-destructive reading of the electric responses of pixels of a region of interest;
   2.2) determining an evolution of a spatial distribution of pixels in logarithmic mode with respect to a previous iteration on the basis of the electric responses of the pixels of the region of interest, said evolution representative of a fluctuation in a wavefront of the incident light flux between this iteration and the previous iteration;
   2.3) based on said evolution, establishing a command for the wavefront correction element in order to correct the wavefront of the light flux;
   2.4) configuring the wavefront correction element through the command,
   3) reading the electric responses of the pixels of the matrix of pixels resulting in the image.

2. The method of claim 1, comprising a prior step of resetting pixels of the matrix before step 1).

3. The method of claim 1, wherein of the spatial distribution of pixels in the logarithmic mode comprising identifying said pixels in the logarithmic mode, said identifying comprising comparing between each one of the electric responses and a threshold value, a crossing of the threshold value by the electric response of a pixel indicating that said pixel is in the logarithmic mode.

4. The method of claim 1, wherein determining the evolution of the spatial distribution of pixels in the logarithmic mode comprises identifying pixels in the logarithmic mode and a comparison between positions of these pixels in the logarithmic mode with positions of pixels in the logarithmic mode during the previous iteration.

5. The method of claim 4, wherein determining the evolution of the spatial distribution of pixels in logarithmic mode comprises identifying a contour that separates the pixels in logarithmic mode and the pixels in linear mode, and the comparison between the position of the contour and the preceding position of the contour during the previous iteration.

6. The method of claim 1, wherein the command of the wavefront correction element is determined so as to stabilise the spatial distribution of pixels in logarithmic mode between two iterations.

7. The method of claim 1, wherein the region of interest groups together less than half of the pixels of the matrix.

8. The method of claim 1, wherein the method comprises at least five iterations implementing steps 2.1) to 2.4).

9. The method of claim 1, wherein the region of interest is defined prior to the exposure of the pixels.

10. The method of claim 1, comprising a prior step of identifying the region of interest intervening between step 1) and step 2), wherein the region of interest is determined after the non-destructive reading of the electric responses of all the pixels, the region of interest being defined to group together a set of pixels having electric responses on average greater than electric responses of pixels outside the region of interest.

11. The method of claim 1, wherein during step 2.1), the electric responses of the other pixels outside the region of interest are not read.

12. Non-transitory computer-readable medium having program code instructions recorded thereon that can be used in a computer for the execution of the steps of a method according to claim 1 when said program is executed on a computer using said non-transitory medium.

13. Image acquisition system comprising:
   an imager comprising a matrix of pixels in photovoltaic mode configured to generate an electric response when exposed to an incident light flux, the imager being adapted to allow for a non-destructive reading of the electric response of pixels during the exposure,
   an optical path leading to the imager,
   a wavefront correction element arranged in the optical path downstream from the imager, a data processing unit configured to implement steps 2.1) to 2.4) of claim 1.

\* \* \* \* \*